(12) United States Patent
Luriya et al.

(10) Patent No.: US 6,861,060 B1
(45) Date of Patent: Mar. 1, 2005

(54) PERSONAL CARE FORMULATIONS

(76) Inventors: Elena Luriya, 8/17 Naftali Ben Efraim, Rehovot 76217 (IL); Leonid Luriya, 8/17 Naftali Ben Efraim, Rehovot 76217 (IL)

( * ) Notice: Subject to any disclaimer, the term of this patent is extended or adjusted under 35 U.S.C. 154(b) by 0 days.

(21) Appl. No.: 09/557,098

(22) Filed: Apr. 21, 2000

(51) Int. Cl.[7] .................. A61K 9/00; A61K 9/02; A61K 9/10

(52) U.S. Cl. .......... 424/400; 424/401; 424/405; 424/427; 424/430; 424/434; 424/435; 424/436; 424/49; 424/53; 514/937

(58) Field of Search ................. 424/450, 400, 424/401, 427, 430, 434, 435, 436, 49, 53, 835; 504/937–943

(56) References Cited

U.S. PATENT DOCUMENTS

| | | | |
|---|---|---|---|
| 4,670,185 A | | 6/1987 | Fujiwara et al. ............ 252/311 |
| 4,767,615 A | | 8/1988 | Geho et al. .................. 424/57 |
| 4,894,220 A | * | 1/1990 | Nabi |
| 5,128,139 A | | 7/1992 | Brown et al. ............... 424/450 |
| 5,338,761 A | * | 8/1994 | Nakajima |
| 5,376,646 A | * | 12/1994 | Pittrof |
| 5,415,867 A | | 5/1995 | Minchey et al. ............ 424/450 |
| 5,443,840 A | | 8/1995 | Morancais et al. ......... 424/450 |
| 5,576,016 A | | 11/1996 | Amselem et al. ........... 424/450 |
| 5,626,868 A | | 5/1997 | Morancais et al. ......... 424/450 |
| 5,662,932 A | * | 9/1997 | Amselem |
| 5,679,374 A | | 10/1997 | Fanchon et al. ............ 424/450 |
| 6,117,415 A | * | 9/2000 | Schwarz |

FOREIGN PATENT DOCUMENTS

| | | | | |
|---|---|---|---|---|
| WO | 88/00824 | * | 2/1988 | |
| WO | WO92/03121 | | 5/1992 | .......... A61K/9/107 |

* cited by examiner

*Primary Examiner*—Gollamudi S. Kishore
(74) *Attorney, Agent, or Firm*—Greenberg Traurig LLP; Eugene C. Rzucidlo

(57) ABSTRACT

Personal care and hygiene formulations for topical application to mucosal surfaces. These formulations include an amphiphilic lipid carrier in the form of a colloidal composition which can include a micellar aggregate or mixed micelles dispersed in a continuous aqueous phase, or an emulsion of lipid droplets suspended in a continuous aqueous phase, and an active agent which is an anti-microbial agent. The lipid carrier has high adhesiveness to mucous membranes such as the soft tissues of the oral cavity. The lipid carrier also has a high load capacity for the active agent to be carried to these tissues. These formulations have the desirable properties of carrying a large amount of active agent for controlled and prolonged release thereof at the desired site, such as mucous membrane surfaces and surrounding tissue. Accordingly, the present invention provides a formulation for oral or topical application including an anti-microbial agent and a lipid. The agent is held by the carrier through a hydrophobic interaction and is released from the carrier in a controlled manner over a prolonged period of time. The lipid is also characterized by having a high adhesive capability towards mucous membrane surfaces. The lipid and the agent are preferably present in a ratio in a range of from about 1:10 to 10:1, more preferably from about 1:5 to about 5:1, and most preferably from about 1:3 to about 3:1 in the formulation.

21 Claims, 1 Drawing Sheet

PERSONAL CARE FORMULATIONS

FIELD AND BACKGROUND OF THE INVENTION

The present invention relates to new improved formulations for application to a mucosal tissue, and to methods of preparation of these formulations. These formulations are useful for oral administration, such as mouth wash or oral rinse formulations. More specifically, the present invention concerns improved formulations including a lipid carrier and biologically active agent dispersed in a continuous aqueous phase. The lipid carrier is characterized by having high adhesive capabilities towards mucous membranes such as those of the gums, tongue and palate. The lipid carrier also has a high load capacity for the biologically active agent. As such, the lipid carrier can specifically target a relatively large amount of the agent to these mucous membranes to ensure a controlled and sustained release of the agent at the mucous surface.

In the field of personal care and hygiene, many different formulations have been designed and employed commercially in a wide variety of "over-the-counter" medications and products for a number of purposes including oral hygiene and skin care. Many of these medications and products contain both a biologically active agent such, as for example, an anti-microbial agent, and an inert vehicle. The particular choice of vehicle depends upon the desired properties of the formulation.

However, the currently available formulations for personal care and hygiene products suffer from a number of drawbacks, including lack of suitability of the carrier for its intended use. Most of these known formulations suffer from an inability to carry a large amount of the active agent and to ensure a controlled and prolonged release thereof at the desired site. This inability is particularly undesirable, since usually any biologically active agent must remain at the desired site for a prolonged period in order to be effective.

Recently, liposome-based delivery systems have been developed in which the active agent is encapsulated within a multilamellar lipid vesicle or liposome, and is then released in a controlled fashion from the liposome. For example, U.S. Pat. No. 4,588,578 discloses lipid vesicles in which the active ingredient is encapsulated, rather than being complexed with a lipid. However, such liposomes suffer from the drawback of having a limited load capacity for the active agent.

Furthermore, many of these liposomes and related lipid particles are not suitable for long term storage, particularly at ambient temperatures. An example of a liposome-based delivery system has been disclosed in U.S. Pat. No. 4,767,615, in which specific modifications to the lipid structure enable specific targeting of the liposome to specific tissues, such as the enamel of the teeth. Conversely, the very specificity of such carriers limits them to tissues covered by an enamel layer. Furthermore, the maximum capacity for the active agent is only about 20% of the liposome volume of the disclosed prior art carrier.

As another example, U.S. Pat. No. 5,415,867 discloses lipid particles with a relatively high ratio of agent to lipid. However, this reference does not teach or disclose the use of such particles for administration to a mucosal tissue or mucous membrane. Instead, the reference primarily teaches parenteral administration. Similarly, PCT Application No. WO 92/03121 discloses only colloidal particles for oral administration or for administration on the intact skin. Thus, the prior art does not teach the use of high ratio lipid particles for administration to a mucous membrane or mucosal surface.

Furthermore, the known non-liposome, hydrophilic, water soluble formulations also suffer from a very short retention time at the tissue to which they are applied, because they are readily washed away or degraded.

In view of the above drawbacks of the prior art carriers, there has been a long-felt need to provide formulations for personal care and hygiene which are multi-purpose and can be applied to a mucosal tissues. Such carriers must have high adhesion capability to ensure contact for a prolonged time, and must be able to carry a high amount of active agent to the site of adhesion for a controlled and prolonged release to the desired tissue.

Other aims and aspects of the present invention will be apparent from the following description of the present invention.

SUMMARY OF THE INVENTION

The present invention concerns new personal care and hygiene formulations for topical application to mucosal surfaces. These formulations include an amphiphilic lipid carrier in the form of a colloidal composition which can include a micellar aggregate or mixed micelles dispersed in a continuous aqueous phase, or an emulsion of lipid droplets suspended in a continuous aqueous phase, and an active agent which is an anti-microbial agent. The lipid carrier has high adhesiveness to mucous membranes such as the soft tissues of the oral cavity. The lipid carrier also has a high load capacity for the active agent to be carried to these tissues.

These formulations have the desirable properties of carrying a large amount of active agent for controlled and prolonged release thereof at the desired site, such as mucous membrane surfaces and surrounding tissue. Accordingly, the present invention provides a formulation for oral or topical application including an anti-microbial agent and a lipid. The agent is held by the carrier through a hydrophobic interaction and is released from the carrier in a controlled manner over a prolonged period of time. The lipid is also characterized by having a high adhesive capability towards mucous membrane surfaces. The lipid and the agent are preferably present in a ratio in a range of from about 1:10 to about 10:1, more preferably from about 1:5 to about 5:1, and most preferably from about 1:3 to about 3:1 in the formulation.

According to the present invention, there is provided a formulation for topical application to a tissue selected from the group consisting of nasal, ophthalmic, oral cavity, vaginal and rectal, the formulation including: (a) a biologically active agent selected from the group consisting of antibiotic, antiviral agent, antifungal agent, disinfectant, nutrient, anti-inflammatory agent, local anesthetic and essential oil; and (b) a lipid carrier, the lipid carrier including at least one lipid selected from the group of amphiphilic phospholipids consisting of egg yolk lecithin, phosphatidic acid, alkylphosphates, phosphatidylglycerol, Soya lecithin and phosphatidyl choline, the lipid being characterized as a colloidal dispersion or as an emulsion of lipid droplets in suspension in an aqueous medium, and the lipid and the active agent being present in a ratio of from about 10:1 to about 1:10, such that the agent is carried by the lipid carrier and the agent is released from the carrier in a controlled manner and over a prolonged period of time.

Hereinafter, the term "topical" refers to direct application to an external surface or to a cavity of tissues of the body.

The term "ophthalmic" refers to the tissue at the external surface of the eye or the external surfaces of surrounding tissues. The term "oral cavity" includes the surface of the mouth, lips, tongue and gums.

Preferably, the antibiotic is selected from the group consisting of erythromycin, tetracycline, and chloramphenicol. Preferably, the antiviral agent is selected from the group consisting of azothymidin, acyclovir, dideoxyuridine and amantadine. Preferably, the antifungal agent is selected from the group consisting of ketoconazole, fluconazole, miconazole, tolnaftate, amphotericin and nystatin. Preferably, the disinfectant is selected from the group consisting of chlorhexidine and salts thereof, triclosan, cetrimide and cetylpyridinium chloride. Preferably, the nutrient is selected from the group consisting of vitamin A, vitamin E, vitamin D, vitamin K, ascorbyl palmitate, coenzyme Q-10, coenzyme Q-50, lipoic, biotin and carnitine. Preferably, the anti-inflammatory agent is selected from the group consisting of non-steroidal and steroidal. More preferably, the non-steroidal anti-inflammatory agent is selected from the group consisting of indomethacin, ketoprofen, diclofenol and acetylsalicylic acid. Alternatively and more preferably, the steroidal anti-inflammatory agent is selected from the group consisting of dexamethazone, prednisolone and fluoromethzolone acetonide. Preferably, the local anesthetic is selected from the group consisting of lidocaine, trimecaine and benzocaine. Preferably, the essential oil is selected from the group consisting of menthol, vanillin, peppermint oil, clove oil, eucalyptus oil and lavender oil.

Preferably, the agent is further characterized by having activity in the oral cavity for treatment of at least one condition selected from the group consisting of gum disease, caries, dry mouth, malodorous breath, and microbial infection. More preferably, the microbial infection includes an infection selected from the group consisting of bacterial, viral and fungal.

Alternatively and preferably, the agent is further characterized by having activity on a tissue selected from the group consisting of vaginal and rectal, the activity being suitable for treatment of at least one condition selected from the group consisting of inflammation, irritation, dryness and microbial infection.

According to other preferred embodiments of the present invention, the lipid and the agent are present in a ratio of from about 5:1 to about 1:5. More preferably, the lipid and the agent are present in a ratio of from about 3:1 to about 1:3.

According to a preferred embodiment of the present invention, the formulation preferably further includes a stabilizer, the stabilizer including at least one surfactant selected from the group consisting of non-ionic, anionic, cationic and amphiphilic. Preferably, the stabilizer is a non-ionic surfactant selected from the group consisting of polyethylene glycol derivatives and glycerol derivatives. More preferably, the polyethylene glycol derivative is selected from the group consisting of Tweens, tritons, tyloxapol, pluronics, Brijes, Spans, poloxamers and emulphors. Also more preferably, the glycerol derivative is selected from the group consisting of polyglycerines and polyalkylglycerides.

Alternatively and preferably, the stabilizer is an anionic surfactant selected from the group consisting of alkyl and aryl sulphonates and phosphates. Also alternatively and preferably, the stabilizer is a cationic surfactant selected from the group consisting of cethyl pyridinium chloride or bromide, and cethyl trimethylammonium bromide. Alternatively and preferably, the stabilizer is an amphiphilic surfactant selected from the group consisting of alkyl betaine derivatives, cocoamphodiacetale derivatives, lauroamphoacetates and phosphatidylglycerol.

According to another preferred embodiment of the present invention, the formulation preferably also includes at least one lipid additive selected from the group consisting of triglycerides, alkyl esters, cholesterol, triolein, edible oils, medium chain glycerides, isopropylmyristate and cholesterol esters.

According to still another preferred embodiment of the present invention, the formulation further includes at least one additive selected from the group consisting of flavors, aroma modifiers, sweeteners, colors, and antioxidants.

According to yet another preferred embodiment of the present invention, the formulation includes a lipid in a form selected from the group consisting of micelles, mixed micelles and micellar aggregates, the lipid having a particle size of from about 10 to about 300 nm. Alternatively and preferably, the lipid is in a form selected from the group consisting of an emulsion and a suspension, the lipid having lipid particles of size in the range of from about 50 to about 300 nm.

According to another embodiment of the present invention, there is provided a method for the preparation of a formulation for topical application to a tissue selected from the group consisting of ophthalmic, oral cavity, vaginal and rectal, the method including the steps of: (a) dissolving the lipid and the agent in a water-miscible solvent to form a solution; and (b) adding water to the solution in an amount sufficient to dilute the water-miscible solvent to form a diluted solution. Preferably, the water-miscible solvent is selected from the group consisting of ethyl alcohol, propylene glycol and polyethylene glycol (PEG). Also preferably, the method further includes the step of: (c) passing the diluted solution through a microporous membrane having a pore size selected from the group consisting of 0.05 micron, 0.1 micron, 0.2 micron, 0.45 micron and 0.8 micron.

According to still another embodiment of the present invention, there is provided a method for the preparation of a formulation for topical application to a tissue selected from the group consisting of ophthalmic, oral cavity, vaginal and rectal, the method including the steps of: (a) mixing the lipid and the agent to form a substantially clear solution; (b) mixing the clear solution with water to form a diluted suspension; and (c) sizing the diluted suspension to form a homogenized suspension. Preferably, the method further includes the step of: (d) filtering the homogenized suspension with a microfilter.

According to yet another embodiment of the present invention, there is provided a method of administering a formulation to a mucosal tissue selected from the group consisting of nasal, ophthalmic, oral cavity, vaginal and rectal, comprising the steps of: (a) providing the formulation, the formulation featuring: (i) a biologically active agent selected from the group consisting of antibiotic, antiviral agent, antifungal agent, disinfectant, nutrient, anti-inflammatory agent, local anesthetic and essential oil; and (ii) a lipid carrier, the lipid carrier including at least one lipid selected from the group of amphiphilic phospholipids consisting of yolk lecithin, Soya lecithin, phosphatidylglycerol and analogs thereof, the lipid being characterized as a colloidal micellar dispersion or as an emulsion of lipid droplets dispersed in an aqueous medium, and the lipid and the agent being present in a ratio of from about 10:1 to about 1:10, such that the agent is carried by the lipid of the lipid carrier and the agent is released from the lipid in a controlled manner and over a prolonged period of time, and such that the lipid carrier has a property of high adhesion to the mucosal tissue; and (b) administering the formulation to the mucosal tissue. Preferably, the mucosal tissue is the oral cavity and the formulation is administered as a mouthwash.

BRIEF DESCRIPTION OF DRAWING

The invention is herein described, by way of example only, with reference to the accompanying drawing, wherein.

DETAILED DESCRIPTION OF THE INVENTION

Figure 1:
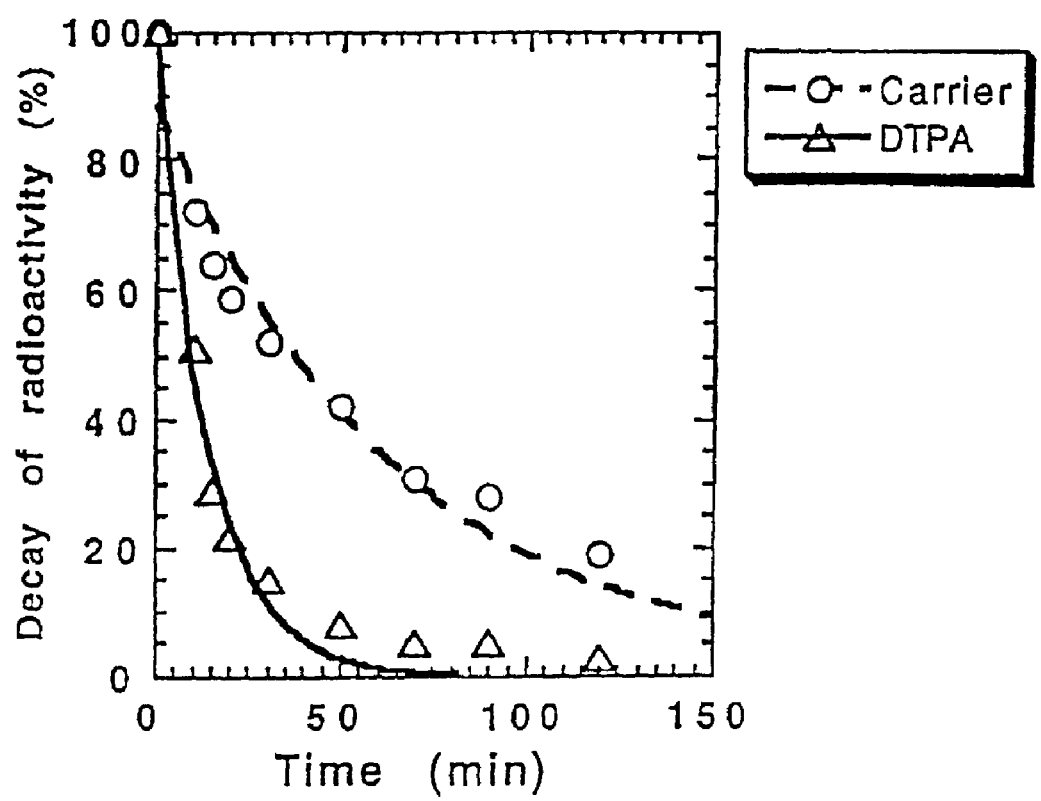
FIG. 1 is a graph of the effect of the formulation of the present invention.

The present invention concerns new improved formulations for local oral and other topical mucosal applications which contain a biologically active agent. These formulations are therefore particularly useful for the purposes of oral hygiene and for the purposes of antiseptic treatment of the mucosal surface.

More specifically, the present invention concerns formulations containing micelles or self-emulsifying compositions having a biologically active agent, which have a high adhesive capacity for mucous membranes such as those on the outer surfaces of the gums. These colloidal compositions also have a large capacity for the anti-microbial agent. The lipid components of the micelles or emulsion interact with the agent through non-covalent hydrophobic attraction.

The formulations of the present invention are particularly well suited for administering the anti-microbial agent in effective amounts to mucosal surfaces where the agent is released by a slow-release process over a prolonged period. These formulations are useful as mouth wash formulations for oral hygiene. After contacting the oral cavity, the carrier with the anti-microbial agent will first adhere to the mucosal surface of the gums, and the agent will then be released to the surrounding teeth and oral cavity in a substantially continuous manner over a prolonged time. Indeed, effective amounts of the anti-microbial agent could potentially be present for as long as 24 hours, requiring oral application of the formulation only about once a day. Such oral formulations are therefore effective for maintaining general oral hygiene and specifically to combat tooth decay, gum disease and malodorous breath.

These desirable characteristics of the formulations of the present invention were achieved by preparing a formulation in which the ratio of lipid to biologically active agent was reduced from prior art formulations, which relied heavily on employing large amounts of lipid to carry effective amounts of the active ingredient. In addition, the lipid carrier is needed to target the active agent and cause it to adhere to the desired tissue, and then to release this agent in a controlled manner. Prolonged, controlled release of the biologically active agent is especially important because such release of such a biologically active agent provides for optimal biological effects and, at the same time, also reduces the absolute amount of the agent necessary for the desired effect. Reduction of the total amount of the active ingredient could decrease adverse side effects, which are usually dose dependent.

Although the Examples are drawn to specific active ingredients, namely chlorhexidine and triclosan, these are for illustrative purposes only and are not meant to be limiting. It is anticipated that formulations according to the present invention would also be effective for a number of other active ingredients, which can be divided into the following groups: antibiotic, antiviral agent, antifungal agent, disinfectant, nutrient, anti-inflammatory agent, local anesthetic and essential oil.

Examples of each of these groups are listed herein, it being understood that these examples are for illustrative purposes only and are not meant to be limiting in any way. Preferably, the antibiotic is selected from the group consisting of erythromycin, tetracycline, and chloramphenicol. Preferably, the antiviral agent is selected from the group consisting of azothymidin, acyclovir, dideoxyuridine and amantadine. Preferably, the antifungal agent is selected from the group consisting of ketoconazole, fluconazole, miconazole, tolnaftate, amphotericin and nystatin. Preferably, the disinfectant is selected from the group consisting of chlorhexidine and salts thereof, triclosan, cetrimide and cetylpyridinium chloride. Preferably, the nutrient is selected from the group consisting of vitamin A, vitamin E, vitamin D, vitamin K, ascorbyl palmitate, coenzyme Q-10, coenzyme Q-50, lipoic, biotin and carnitine. Preferably, the anti-inflammatory agent is selected from the group consisting of non-steroidal and steroidal. More preferably, the non-steroidal anti-inflammatory agent is selected from the group consisting of indomethacin, ketoprofen, diclofenol and acetylsalicylic acid. Alternatively and more preferably, the steroidal anti-inflammatory agent is selected from the group consisting of dexamethazone, prednisolone and fluoromethzolone acetonide. Preferably, the local anesthetic is selected from the group consisting of lidocaine, trimecaine and benzocaine. Preferably, the essential oil is selected from the group consisting of menthol, vanillin, peppermint oil, clove oil, eucalyptus oil and lavender oil.

The formulations of the present invention preferably have a ratio of biologically active agent to lipid of from about 1:10 to about 10:1, more preferably of from about 1:5 to about 5:1 and most preferably from about 1:3 to about 3:1. The high mucosal adhesive property of this delivery system is determined by the lipid molecules at the surface of the particles. Optionally and preferably, there is also included stabilizing agents, in the form of anionic and non-ionic surfactants, which serve to stabilize the lipid-biologically active agent complex at the desired ratio.

Preferred formulations of the present invention include those having chlorhexidine or triclosan as the biologically active agent, which in their case, serve as anti-microbial agents. These preferred formulations are intended primarily for personal hygiene products including mouth washformulations and chewing gum, and cosmetic products including various formulations and liquid soaps.

In the preferred formulations of the invention, the lipid component is in the form of micelles, mixed micelles or micellar aggregates, or in the form of emulsions (lipid colloids with an inner lipid phase or fatty phase) which provide for only an external association between the lipid and the biologically active agent, as opposed to liposomes which have a structure consisting of an inner hydrophilic core which contains the biologically active agent. The interaction between the biologically-active agent and the lipid is via hydrophobic interactions Such interactions therefore enable the lipid to associate with a large amount of biologically active agent over the entire surface of the lipid micelle or emulsion to provide a high load capacity for the biologically active agent of at least about 10% and up to about 90%, more preferably at least 25% and up to about 80%, of the weight of the lipid phase. The lipid itself causes the strong adhesion of the dispersed formulation to the mucous membranes of the oral cavity and to other mucosal tissues. Without wishing to be bound by a particular mechanism, presumably the adhesive property of the formulation is due to the amiphiphilic characteristics of the lipid.

For example, in mouth wash formulations in accordance with the present invention, the lipid-biologically active agent ratio is of such a nature that a single use of the mouth wash solution will provide gum and teeth protection, and prevent the occurrence of malodorous breath for approximately a full day (24 hours), even if the user eats and drinks during this period. In addition to the above essential components of the formulations, stabilizers (preferably anionic and non-ionic surfactants) are also preferably employed to stabilize the interaction between the lipid and biologically active agent, which enables maximum loading of the lipid micelles or emulsions with the biologically active agent, as well as stabilization of the release of the biologically active agent at the desired site.

The lipid components of the formulations of the present invention, whether in the form of micelles, mixed micelles or micellar aggregates, or emulsions, are organized into aggregates of particular size distribution of from about 10 nm to about 300 nm, this providing the above noted high adhesion capability of the lipid aggregates to mucosal membranes and enabling both a high load capability of the biologically active agent onto the lipid aggregates and a prolonged release period of the biologically agents from the lipid aggregates. The structure of the lipid aggregates includes hydrophobic hydrocarbon chains of the lipid molecules at the core and polar groups of the lipid molecules at the surface, thereby enabling these lipid aggregates to be formulated into the preferred aqueous formulations of the present invention. Also, the structure provides for effective interaction with the preferred biologically active agents of the present invention. The improved properties of this formulation over previously known formulations are achieved by forming the suspension with lipid or lipophilic particles which are highly adhesive to mucosal membranes, and which permit prolonged and controlled release of the biologically active agent from the lipid particles at the mucosal surface.

More preferably, the formulation is an aqueous lipid colloidal formulation for application to a mucosal surface, in a particular, an oral mucosal membrane surface as found on the gums. This formulation includes a pharmaceutically acceptable anti-microbial agent that is distributed between an aqueous phase and suspended small water-insoluble particles in a colloidal dispersion.

The preparation of the formulations of the present invention includes well known standard chemical techniques well known to those of skill in the art as set forth in a large number of chemical texts readily available to skilled artisans.

As the formulations of the present invention are preferably non-medical formulations intended for over-the-counter distribution to the public, the ingredients of the formulations of the present invention have preferably been approved for this purpose by the relevant health authorities. Examples of the various components of the formulations of the present invention are the following.

First, lipids which have high adhesive capability to mucosal membranes include the various amphiphilic lipids such as the phospholipids, for example, egg yolk lecithin, Soya lecithin and phosphatidylcholine. Preferably such lipids will be used at a concentration of from about 0.1 to about 5% in the formulations. At this concentration an optimally bioadhesive particle will be obtained.

Suitable biologically active agents include agents which can be used to treat an existing condition of the skin, or of the rectal, vaginal or oral cavities, or to prevent such a condition from arising as a prophylactic measure. For example, preferably the agent is further characterized by having activity in the oral cavity for treatment of at least one condition selected from the group consisting of gum disease, caries, dry mouth, malodorous breath, and microbial infection. Hereinafter, any agent which is active against a microbe is referred to as an "anti-microbial agent". Hereinafter, the term "microbial infection" includes bacterial, viral and fungal infections.

Alternatively and preferably, the biologically active agent is suitable for treatment of at least one condition selected from the group consisting of inflammation, irritation, dryness and microbial infection on a tissue selected from the group consisting of vaginal and rectal.

If an anti-microbial agent is to be used, suitable anti-microbial agents include the known, approved, multi-purpose agents included with various liquid antiseptics and disinfectants, such as triclosan and chlorhexidine. Preferably, triclosan is used in a concentration of from about 0.01% to about 2.0% in the final formulations, and chlorhexidine is used in a concentration of from about 0.001% to about 2% in the final formulations, when these formulations are ready for administration.

It should be noted that the two essential ingredients are the lipid and the biologically active agent. However, additional ingredients may be optionally added to the formulation to achieve certain desired characteristics. According to a preferred embodiment of the present invention, a suitable stabilizer is preferably included. Stabilizers of the lipid and anti-microbial agent complex are generally surfactants which stabilize the interaction between the lipids and the anti-microbial agent in the formulations. These stabilizers thus serve to increase the load capability of the lipids, control the release of the active agent from the lipids over a long period, and also improve the reological properties of the formulations (viscosity of the formulations). The surfactants may be of a number of types, including non-ionic surfactants such as polyethylene glycol derivatives and glycerol derivatives. The polyethylene glycol derivatives can be, for example, polyoxyethylated including the various Tweens, tritons, tyloxapol, pluronics, Brijes, Spans, poloxamers, and emulphors. The glycerol derivatives can be for example, polyglycerines or polyalkylglycerides. When such non-ionic surfactants are used in the formulations, the concentration is preferably in the range of from about 0 to about 5%. These non-ionic surfactants are particularly useful for improving the reological properties (viscosity) and stability of the formulations.

Suitable anionic surfactants include the various alkyl and aryl sulphonates and phosphates such as, for example, the various stearates (e.g. sodium lauryl sulfate), oleates or palmitates. When those are used in the formulations, their concentration is preferably in the range of from about 0 to about 0.5%. These anionic surfactants are particularly useful for improving the loading of the anti-microbial agent onto the lipid particles in the formulations. Furthermore, in this colloidal composition, the addition of anionic surfactants such as sodium stearate does not detract from the activity of chlorhexidine. Such a finding is contrary to the teachings of the prior art, in which the addition of anionic surfactants to prior art formulations of chlorhexidine resulted in a loss of activity.

Suitable cationic surfactants include cethyl pyridinium chloride or bromide, or cethyl trimethylammonium bromide, preferably at a concentration in the range of from about 0 to about 2%. These cationic surfactants are particularly useful for improving the antiseptic activities of triclosan or chlorhexidine in the formulations.

Suitable amphiphilic surfactants include the various alkyl betaines, cocoamphodiacetales or lauroamphoacetates, as well as phosphatidylglycerol. Preferably, the concentration is in the range of from about 0 to about 2%.

It should be noted that a mixture of two or more of the above surfactants may be used in the formulations of the present invention, which is preferred, each surfactant improving the properties of the formulation in its own specific way.

An additional optional ingredient is an additional lipid moiety. Suitable lipid moieties include the various triglycerides, alkyl esters and cholesterol, such as, for example, triolein, Soya oil, miglyol; isopropylmyristate; and cholesterol esters. Preferably, the concentration is in the range of from about 0 to about 30%. These additives are particularly useful in the preparation of emulsions and serve to increase the total amount of the active agent carried by the lipid particles.

Another optional but preferred ingredient is a flavor or aroma modifier. Suitable flavor or aroma modifiers include the various approved natural or synthetic flavoring or aroma substances such as, for example, vanillin, menthol, peppermint oil, thyme oil and the like. When used in the formulations, their amount is that quantity specified by the manufacturer or as acceptable in the art. These additives are particularly useful in those formulations of the invention intended for use as oral formulations such as a mouth wash, oral rinse or the like.

Still another optional ingredient is a sweetener. Suitable sweeteners include the various food grade sweeteners such as aspartame, sorbitol, glycerol, mannitol, saccharine, cyclamates and the like. When used their amount is usually specified by the manufacturer or as acceptable in the art. These additives are particularly useful in the oral formulations of the invention.

Other optional ingredients include a coloring agent. Suitable coloring agents include the various food grade colors, such as, for example, beta-carotene, methylene blue and the like. When used, their amount is that specified by the manufacturer or as acceptable in the art. These additives are particularly useful in oral formulations of the invention.

Finally, another optional ingredient is an antioxidant. Suitable antioxidants and other stabilizers include the various tocopherols, ascorbates, and helates such as EDTA. Preferably the concentration is in the range of from about 0.001 to about 0.2%. These additives are particularly useful to improve the stability of the formulations during storage and to prolong shelf-life.

As mentioned above, the various lipids, biologically active agents and additives of the formulations of the invention are known and widely available from a member of commercial suppliers. Methods of preparation are also known. However, in accordance with the present invention there is also provided specific preferred methods to prepare these formulations. These methods include processes for the preparation of bioadhesive colloidal antiseptic compositions, which are particularly useful for preparing stable oral rinse formulations. One example of such a method starts with the dissolution of the biologically active agent, the lipid, and any additional ingredients such as stabilizers and antioxidants, in a minimal amount of a water-miscible solvent, such as ethyl alcohol. Next, the ingredients are mixed with an appropriate amount of water.

This will provide the desired suspension of liquid particles as a colloidal dispersion in the water phase with the antiseptic distributed between the water phase and the suspended lipid particles. If necessary, the suspension can be filtered through a microporous membrane, preferably with a pore size of from about 0.1 to about 0.45 microns, to improve the particle size distribution and suspension stability. Alternatively, the raw, original suspension can be treated in any suitable known high pressure homogenizer to reduce particle size as is well known in the art. Following this homogenization step, the suspension can be optionally filtered through a microporous membrane as noted above.

In formulations containing lipid emulsions in which lipid additives are also included, the same procedure as above may be employed to improve and control particle size. In addition, in such formulations a self-dispersion process may be used followed by homogenization of the coarse dispersion to yield the desired submicron colloidal formulation having improved stability.

It should be noted, however, that the optimal method for preparing each formulation of the invention is dependent upon the choice of the ingredients for each formulation and the steps of the method will be chosen accordingly to the properties of the various components, their behavior in solution or suspension and their concentration. Such modifications of the method are readily apparent to those of ordinary skill in the art.

The present invention will now be described in more detail with the following non-limiting Examples.

EXAMPLE 1

Chlorhexidine in Colloidal Composition Without Additional Surfactants 315 mg (~0.4 mmol) of purified egg lecithin (E-80) and 115 mg (~0.18 mmol) of chlorhexidine diacetate were dissolved together in 5 ml of ethyl alcohol while stirring to obtain a stock solution. The stock solution was diluted with distilled water during intensive stirring until 45 ml of water was added, such that the final concentration of ethyl alcohol was 10% to obtain a suspension. The suspension was further filtered through a microporous membrane filter of pore size 0.45 micron to form a stable suspension of uniformly sized particles. The mean particle size was 285±65 nm. About 50% of chlorhexidine was bound to lipid particles, as determined by centrifugal ultrafiltration. The absence of a liposomal fraction in the suspension was determined by NMR.

The high density of lecithin molecules on the particle surface should increase the opportunity for the amphiphilic phosphatidylcholine molecules to interact with polar groups of mucosal tissues. Antimicrobial activity of chlorhexidine was not altered (data not shown).

EXAMPLE 2

Chlorhexidine Colloidal Formulation with Anionic Surfactant 580 mg (0.8 mmol) of lecithin (E-80), 250 mg of chlorhexidine diacetate (0.4 mmol) and 235 mg (0.8 mmol) of sodium lauryl sulfate (SLS) were dissolved in 4 ml of ethyl alcohol. After dilution with 96 ml of distilled water, the resultant suspension was filtered sequentially through membrane filters having a pore size of first 0.45 micron and then 0.22 micron. A stable suspension with particles of a size less than 200 nm was obtained. More than 70% of chlorhexidine was associated with the lipid phase. The antimicrobial activity of chlorhexidine in the prepared colloidal formulation was tested "in vitro" by diffusion in agar plates and by serial dilution. The activity was in the same range as the activity of chlorhexidine in solution.

EXAMPLE 3

Chlorhexidine Colloidal Formulation with Additional Non-ionic Surfactant

A formulation was prepared as in Example 2 with Lecithin E-80, but instead of sodium lauryl sulfate (SLS), 100 mg of polyoxyethylene sorbitan monooleate (Tween-80) was added to the alcohol solution. After dilution and filtration through a 0.22 micron membrane filter, a fine suspension was obtained, with a mean particle size of about 60 nm. About 50% of the total chlorhexidine was associated with lipid particles.

EXAMPLE 4

Chlorhexidine Colloidal Formulation with Additional Anionic and Non-ionic Surfactants, Treated with a High Pressure Homogenizer The formulation was prepared by dissolving 500 mg (0.68 mmol) of lecithin E-80, 125 mg (0.2 mmol) of chlorhexidine diacetate, 120 mg (0.4 mmol) of SLS and 120 mg of Tween-80 in a mixture of 2 ml absolute ethyl alcohol and 3 ml 2-propanediol (propylene glycol) to form a stock solution. The stock solution was diluted with 95 ml of distilled water and 2 g of glycerol was added to form a suspension. The suspension was treated with a high pressure homogenizer (EmulsiFlex® C-5, "Avestin", Ottawa, Canada), 6 cycles at 12000–15000 psi. The final particle size was about 50 nm with 85% of the drug bound to particles.

EXAMPLE 5

Chlorhexidine Mouthwash Colloidal Formulation

A mouthwash (oral rinse) formulation of the present invention was prepared according to the following method. 7.5 g of Lecithin E-80, 625 mg of chlorhexidine diacetate, 525 mg of Tween-80, 250 mg of D,L-Menthol and 30 mg of alpha-tocopherol acid succinate were dissolved in mixture of 20 ml of absolute ethyl alcohol and 10 ml of propylene glycol. The resultant stock solution was mixed with vigorous stirring with 480 ml of distilled water and 10 g of pure glycerol was added as sweetener to obtain a suspension. The suspension was then filtered sequentially first through a 0.45 micron and then through a 0.22 micron PTFE membrane.

EXAMPLE 6

Triclosan Mouthwash Formulation 300 mg of triclosan (1.05 mmol), 2000 mg (2.7 mmol) of phosphatidylcholine, 500 mg (1.7 mmol) of SLS, 300 mg of D,L-Menthol and 42 mg of aspartame were dissolved in 20 ml of absolute ethyl alcohol with slight heating (40° C.). After dissolution, 98 ml of purified water containing 20 mg of EDTA-Na (ethylenediamine tetraacetic acid sodium salt) was added slowly with vigorous stirring. The coarse suspension was treated with a high pressure homogenizer (6 cycles at 800–900 bar, 12000–14000 psi) and then filtered through a 0.22 micron PTFE membrane filter.

About 95% of the total triclosan was found to be associated with lipid particles having a mean size of about 170 nm. The antiseptic activity was unchanged.

EXAMPLE 7

Non-medicated Colloidal Composition for Evaluation of Bioadhesive Behavior in the Oral Cavity 315 mg of pure phosphatidylcholine and 80 mg of polyoxyethylated sorbitan monolaurate (Tween-20) were dissolved in 2 ml of ethyl alcohol to form a solution. The solution was diluted with purified water to a final volume of 100 ml and then passed through a 0.22 micron PTFE membrane filter. The resultant colloidal carrier had a mean droplet size of about 185 nm.

The bioadhesive properties were examined according to the following method, using the radioactive $Tc^{99}$ label, which is safe and approved for human use. The lipid colloidal particles were labeled with $Tc^{99}$ by using potassium pertechnate-$Tc^{99}$, after reduction by $Sn^{2+}$ so that substantially all radioactivity was completely associated with lipid aggregates. A water solution of $Tc^{99}$ complexed with DTPA (Diethylenetriamine pentaacetic acid), in which all radioactivity was in the aqueous phase, was used as a control. 10 ml of either the labeled colloidal composition or the control solution was administered to the oral cavity of the volunteer human subject, and was then expectorated by the subject after a short rinse. As shown in FIG. 1, more than 20% of the radioactive label associated with the colloidal carrier remained attached to gum and palate tissues over 2.5 hours after expectoration. By contrast, the radioactive label level for the control water solution dropped below 20% of its initial value after less than 20 minutes following rinse, and the remaining radioactivity detected was extremely low after this time.

EXAMPLE 8

Chlorhexidine Colloidal Self-emulsifying Antiseptic Composition 450 mg (0.6 mmol) of purified egg lecithin, 150 mg (0.25 mmol) of chlorhexidine diacetate, 150 mg of PEG-10 laurate and 450 mg (0.5 mmol) of triolein were all mixed together and heated to 60° C. for 20 minutes until dissolution. Water was then added to this solution with gentle stirring. Immediately, a fine oil-in-water emulsion was formed. Such emulsions were observed to be stable with final oil phase concentrations of 5%–25%. The resultant emulsion can optionally be treated by sonication, extrusion or high-pressure homogenization to standardize the size of emulsion droplets.

EXAMPLE 9

Triclosan Colloidal Self-emulsifying Antiseptic Composition

A self-emulsifying composition containing 0.03–0.2% triclosan was prepared as described in example 8, except that triclosan was used instead of chlorhexidine diacetate, and 150 mg of Tyloxapol was added instead of PEG-10 laurate. After formation of the emulsion, the mixture was treated by high-pressure homogenization (6 cycles, 800 bar), producing a stable emulsion.

It will be appreciated that the above descriptions are intended only to serve as examples, and that many other embodiments are possible within the spirit and the scope of the present invention.

What is claimed is:

1. A formulation for application to a mucosal tissue, the formulation comprising:

(a) a biologically active agent wherein said biologically active agent is an antibiotic selected from the group consisting of 3-de[(2,6-dideoxy-3-C-methyl-3-O-methyl-,alpha,-L-ribo-hexopyranosyl)oxy]-11 12-dideoxy-6-O-methyl-3-oxo-12,11-[oxycarbonyl[[4-[4-(3-pyridinyl)-1H-imidazol-1-yl]butyl]imino]], [4-S-(4-alpha,4a-alpha,5a-alpha,6-beta,12a-alpha)]-4-(Dimethylamino)-1,4,4a,5,5a,6–11,12a-octahydro-3,6,10,12,12a-pentahydroxy-6-methyl-1,11 dioxo-2-naphthacenecarboxamide, and D-threo-N-dichloracetyl-1-p-nitrophenyl-2-amino-1,3-propanediol; D-)-(threo-2-dichloroacetamido-1-p-nitrophenyl-1,3-propanediol;
  an antiviral agent selected from the group consisting of azothymidine, 2-Amino-1,9-dihydro-9-[(2-hydroxyethoxy)methyl 1}-6H-purin-6-one, dideoxyuridine, and Cis-1-Acetyl-4-[4-[[2-(2,4-dichloro-phenyl)-2-(1H-imidazol-1-ylmethyl)-1,3-dioxo-1an-4-yl]methoxy]-phenyl]piperazine;
  an antifungal agent selected from the group consisting of Cis-1-Acetyl-4-[4-[[2-(2,4-dichlorophenyl)-2-(1H-imidazol-1-ylmethyl)-1,3-dioxolan-4-yl]methoxy]phenyl]piperazine, 1H-1,2,4-Triazole-1-ethanol, alpha(2,4-difluorophenyl)-alpha-(1H-1,2,4-triazol-1-ylmethyl)-2-(2,4-Difluorophenyl)-1,3.bis(1H-1,2,4-triazol-1-yl)-2-propanol alpha-(2,4-Difluorophenyl)-alpha-(1H-1,2,4-triazol-1-ylmethyl)-1H-1,2,4-triazole-1-ethanol, 1-[2,4-dichloro-beta-[(2,4-dichlorobenzyl)oxy [phenethyl] imidazole, Methyl-(3-methylphenyl)carbamothioic acid O-2-naphthalenyl ester, Polyene antibiotic produced by Streptomycetes nodosus M4575, and 2-Deoxy-4-O-(2,6-diamine-2,6-dideoxy-alpha-D-glucopyranosyl)-D-strePtamine;
  a disinfectant selected from the group consisting of N N"-Bis(4-chlorophenyl)-3,12-diimino-2,4,11 13-tetraazatetradecanediimidamide; 1,1'-hexamethylenebis[5-(p-chlorophenyl)biguanide], chlorhexidine salts, 5-Chloro-2-(2,4-dichlorophenoxy)phenol, centrimide, and 1-Hexadecylpyridinium chloride;
  an anti-inflammatory agent is selected from the group consisting of non-steroidals and steroidals;
  a local anesthetic selected from the group consisting of omega-diethylamino-2,6-dimethylacetanilide, trimecaine, and 4-aminobenzoic acid ethyl ester;
  an essential oil selected from the group consisting of menthol, vanillin, peppermint oil, clove oil, eucalyptus oil and lavender oil; and
(b) a lipid carrier, said lipid carrier having the property of adhesion capacity to mucosal tissue, said lipid carrier including at least one lipid selected from the group of amphiphilic phospholipids consisting of yolk lecithin, Soya lecithin phosphatidylglycerol and analogs thereof said lipid being characterized as mixed micelles dispersed in an aqueous medium, and said lipid and said biologically active agent being present in a ratio of from about 10:1 to about 1:10.

2. The formulation of claim 1, wherein said non-steroidal anti-inflammatory agent is selected from the group consisting of 1-(4-Chlorobenzoyl)-5-methoxy-2-methyl-1H-indole-3-acetic acid, (RS)-2-(3-benzoylphenyl)propionic acid, [o-(2,6-dichloroanilino)phenyl]acetic acid sodium salt, and 2-acetoxybenzoic acid.

3. The formulation of claim 1, wherein said steroidal anti-inflammatory agent is selected from the group consisting of (11-beta, 16-alpha) 9-Flouro-11,17,21-trihydroxy-16-methylpregna-1,4-diene-3,20-dione, (11-beta)-11,17,21-Trihydroxypregna-1,4-dione, 21-desoxy-9alpha-flouro-6alpha-methylprednisolone.

4. The formulation of claim 1, wherein said biologically active agent is further characterized by having activity in the oral cavity, said activity being suitable for treatment of at least one condition selected from the group consisting of gum disease, caries, dry mouth, malodorous breath, and microbial infection.

5. The formulation of claim 1, wherein said biologically active agent is further characterized by having activity on a tissue from the group consisting of nasal, ophthalmic, vaginal, and rectal, said activity being suitable for treatment of at least one condition selected from the group consisting of inflammation, irritation, dryness, and microbial infection.

6. The formulation of claim 5, wherein said microbial infection is selected from the group consisting of bacterial, viral, and fungal.

7. The formulation of claim 1, wherein said lipid in (b) and said biologically active agent in (a) are present in a ratio from about 5:1 to about 1:5.

8. The formulation of claim 7, wherein said lipid and said agent are present in a ratio from about 3:1 to about 1:3.

9. The formulation of claim 1, further comprising a stabilizer, said stabilizer having at least one surfactant selected from the group consisting of non-ionic, anionic, cationic, and amphilic.

10. The formulation of claim 9, wherein said non-ionic surfactant is selected from the group consisting of a polyethylene glycol derivative and a glycerol derivative.

11. The formulation of claim 10, wherein said polyethylene glycol derivative is selected from the group consisting of alpha-Hydro-omega0hydroxypoly-(oxy-1,2-ethanediyl), Polyethylene glycol mono[4-(1,1,3,3-tetramethylbutyl) phenyl]ether, O-3-Amino-3-deoxy-D-glucopyranosyl-(14)-O-[2,6,diamino-2,3,6-trideoxy-D-ribo-hexopyransol-(16)]-2-deoxy-L-streptamine, alpha-hydro-omega-hydroxpoly(oxyethylene)poly(oxypropylene)poly(oxyethylene) block copolymers, Polyethylene glycol fatty alcohol ethers, Sorbitan fatty acid esters, poloxamer, and polyethylene glycol esters of fatty acids.

12. The formulation of claim 10, wherein said glycerol derivative is selected from the group consisting of alpha-hydro-omega-hydroxypoly(oxy-1,2-ethanediyl) and polyalkylglyceride.

13. The formulation of claim 9, where said anionic surfactant is selected from the group consisting of carboxylate, alkyl sulfonate, aryl sulfonate and phosphate.

14. The formulation of claim 9, wherein said cationic surfactant is selected from the group consisting of alkyl pyridinium salt and tetraalkylammonium salt.

15. The formulation of claim 9, wherein said amphiphilic surfactant is selected from the group consisting of alkyl betaine derivative, cocoamphodiacetate derivative, trimyristin, trilaurin, tripalmitin, tristearin, and phosphatidylglycerol.

16. The formulation of claim 1, further comprising at least one lipid additive selected from the group consisting of triglyceride, alkyl ester, cholesterol, octadecenoic acid 1,2, 3-propanetriyl ester, edible oil, tetradecanoic acid 1-methylethyl ester, and methyl ester beta-Cholest-5-en-3-ol.

17. The formulation of claim 1, further comprising at lest one additive selected from the group consisting of flavor, aroma modifier, sweetener, color, and antioxidant.

18. The formulation of claim 1, wherein said lipid in a colloidal dispersion of as form selected from the group consisting of micelles, mixed micelles, and micellar aggregates, said lipid having a particle size of from about 10 to about 300 nm.

19. The formulation of claim 1, wherein said lipid is in the form of a dispersion having liquid particles of size in the range of from about 50 to 300 nm.

20. A method of administering a formulation to a mucosal tissue, comprising the steps of:
(a) providing the formulation, the formulation featuring wherein said biologically active agent is
(i) a biologically active agent which is:
an antibiotic selected from the group consisting of 3-de[(2,6-dideoxy-3-C-methyl-3-O-methyl-, alpha,-L-ribo-hexopyranosyl)oxy]-11 12-dideoxy-6-O-methyl-3-oxo-12,11-[oxycarbonyl[[4-[4-(3-pyridinyl)-1H-imidazol-1-yl]butyl]imino]], [4-S-(4-alpha,4a-alpha,5a-alpha,6-beta,12a-alpha)]-4-(Dimethylamino)-1,4,4a,5,5a,6-11,12a-octahydro-3,6,10,12,12a-pentahydroxy-6-methyl-1,11 dioxo-2-naphthacenecarboxamide, and D-threo-N-dichloracetyl-1-p-nitrophenyl-2-amino-1,3-propanediol; D-)-(threo-2-dichloroacetamido-1-p-nitrophenyl-1,3-propanediol;

an antiviral agent selected from the group consisting of azothymidine, 2-Amino-1,9-dihydro-9-[(2-hydroxyethoxy)methyl 1}-6H-purin-6-one, dideoxyuridine, and Cis-1-Acetyl-4-[4-[[2-(2,4-dichloro-phenyl)-2-(1H-imidazol-1-ylmethyl)-1,3-dioxo-1an-4-yl]methoxy]-phenyl]piperazine;

an antifungal agent selected from the group consisting of Cis-1-Acetyl-4-[4-[[2-(2,4-dichlorophenyl)-2-(1H-imidazol-1-ylmethyl)-1,3-dioxolan-4-yl]methoxy]phenyl]piperazine, 1H-1,2,4-Triazole-1-ethanol, alpha(2,4-difluorophenyl)-alpha-(1H-1,2,4-triazol-1-ylmethyl)-2-(2,4-Difluorophenyl)-1,3 bis(1H-1,2,4-triazol-1-yl)-2-propanol alpha-(2,4-Difluorophenyl)-alpha-(1H-1,2,4-triazol-1-ylmethyl)-1H-1,2,4-triazole-1-ethanol, 1-[2,4-dichloro-beta-[(2,4-dichlorobenzyl)oxy [phenethyl]imidazole, Methyl-(3-methylphenyl) carbamothioic acid O-2-naphthalenyl ester, Polyene antibiotic produced by Streptomycetes nodosus M4575, and 2-Deoxy-4-O-(2,6-diamine-2,6-dideoxy-alpha-D-glycopyranosyl)-D-strePtamine;

a disinfectant selected from the group consisting of N N"-Bis(4-chlorophenyl)-3,12-diimino-2,4,11 13-tetraazatetradecanediimidamide; 1,1'-hexamethylenebis[5-(p-chlorophenyl)biguanide], chlorhexidine salts, 5-Chloro-2-(2,4-dichlorophenoxy)phenol, centrimide, and 1-Hexadecylpyridinium chloride;

an anti-inflammatory agent is selected from the group consisting of non-steroidals and steroidals;

a local anesthetic selected from the group consisting of omega-diethylamino-2,6-dimethylacetanilide, trimecaine, and 4-aminobenzoic acid ethyl ester;

an essential oil selected from the group consisting of menthol, vanillin, peppermint oil, clove oil, eucalyptus oil and lavender oil; and (ii) a lipid carrier, said lipid carrier including at least one lipid selected from the group of amphiphilic phospholipids consisting of yolk lecithin, soya lecithin, phosphatidylglycerol and analogs thereof said lipid being characterized as mixed micelles dispersed in an aqueous medium, and said lipid and said biologically active agent being present in a ratio of from about 10:1 to about 1:10; and (b) administering the formulation to the mucosal tissue.

21. The formulation of claim 5, wherein said microbial infection is selected from the group consisting of bacterial, viral, and fungal.

* * * * *